United States Patent
Reichert

(10) Patent No.: US 10,265,146 B2
(45) Date of Patent: Apr. 23, 2019

(54) SINTER BLANK

(71) Applicant: Amann Girrbach AG, Koblach (AT)

(72) Inventor: Axel Reichert, Widnau (CH)

(73) Assignee: AMANN GIRRBACH AG, Koblach (AT)

( * ) Notice: Subject to any disclaimer, the term of this patent is extended or adjusted under 35 U.S.C. 154(b) by 21 days.

(21) Appl. No.: 15/506,982

(22) PCT Filed: Jul. 1, 2015

(86) PCT No.: PCT/AT2015/000095
§ 371 (c)(1),
(2) Date: Feb. 27, 2017

(87) PCT Pub. No.: WO2016/037199
PCT Pub. Date: Mar. 17, 2016

(65) Prior Publication Data
US 2017/0252134 A1    Sep. 7, 2017

(30) Foreign Application Priority Data

Sep. 12, 2014   (DE) ................. 10 2014 113 148

(51) Int. Cl.
| A61C 13/00 | (2006.01) |
| A61C 13/083 | (2006.01) |
| C04B 35/64 | (2006.01) |
| F27D 5/00 | (2006.01) |
| F27B 17/02 | (2006.01) |

(Continued)

(52) U.S. Cl.
CPC ...... *A61C 13/0022* (2013.01); *A61C 13/0004* (2013.01); *A61C 13/083* (2013.01); *B28B 11/243* (2013.01); *C04B 35/64* (2013.01); *F27B 17/025* (2013.01); *F27D 5/0043* (2013.01);

(Continued)

(58) Field of Classification Search
CPC ............ A61C 13/0022; A61C 13/0004; A61C 13/083
See application file for complete search history.

(56) References Cited

U.S. PATENT DOCUMENTS

| 9,022,784 B2* | 5/2015 | Johansson .......... A61C 13/0004 433/172 |
| 9,918,811 B2* | 3/2018 | Beeby ................ A61C 13/0019 |
| 2006/0082033 A1 | 4/2006 | Hauptmann et al. |

(Continued)

FOREIGN PATENT DOCUMENTS

| DE | 19904523 | 8/2000 |
| DE | 102008002952 | 1/2010 |

(Continued)

OTHER PUBLICATIONS

CopranSintec CoCE Sintermetall-Whitepeaks Dental, CopraSintec K, 2 pages, downloaded on Dec. 10, 2014, http://www.white-peaks-dental.de/sintermetall.php.

*Primary Examiner* — Nathaniel Herzfeld

(74) *Attorney, Agent, or Firm* — Volpe and Koenig, P.C.

(57) ABSTRACT

The invention relates to a sinter blank (1) for producing a dental prosthesis in at least one sintering process, the sinter blank (1) including at least one product area (2), from which the dental prosthesis is produced, and at least one strut (3) that is to be removed after the sintering process, the strut (3) having at least one sliding knob (4) for supporting the strut (3) on a base surface (5) during the sintering process.

15 Claims, 2 Drawing Sheets

(51) Int. Cl.
  *B28B 11/24* (2006.01)
  *G16H 20/40* (2018.01)

(52) U.S. Cl.
  CPC .................. *C04B 2235/6026* (2013.01);
    *C04B 2235/963* (2013.01); *G16H 20/40*
    (2018.01)

(56) References Cited

U.S. PATENT DOCUMENTS

| | | | |
|---|---|---|---|
| 2010/0015570 A1 | 1/2010 | Kutzner et al. | |
| 2010/0291509 A1* | 11/2010 | Berggren | A61C 13/0003 433/199.1 |
| 2010/0323327 A1* | 12/2010 | Eriksson | A61C 13/0022 433/199.1 |
| 2013/0149186 A1 | 6/2013 | Hachenberg et al. | |
| 2014/0087327 A1* | 3/2014 | Noack | A61C 13/0022 433/50 |
| 2015/0327959 A1* | 11/2015 | Hoffmann | A61C 9/002 703/1 |
| 2016/0052055 A1 | 2/2016 | Reichert | |

FOREIGN PATENT DOCUMENTS

| | | |
|---|---|---|
| DE | 102009044461 | 5/2011 |
| DE | 102014106938 | 11/2015 |
| EP | 2014254 | 1/2009 |
| EP | 2602036 | 6/2013 |
| EP | 2792985 | 10/2014 |
| JP | S60102006 | 7/1985 |
| WO | 2014094725 | 6/2014 |

* cited by examiner

SINTER BLANK

BACKGROUND

The present invention relates to a sinter blank for producing a dental prosthesis in at least one sintering process, the sinter blank having at least one product area, from which the dental prosthesis is obtained, and at least one strut, which is to be removed after the sintering process. Moreover, the invention also relates to a sintering chamber and to a computer program for constructing at least one sinter blank.

To produce a dental prosthesis, shaped sinter blanks nowadays often undergo a sintering process such that, as a result of the sintering process, the dental prosthesis is produced, if appropriate after further secondary processing steps, from the sinter blank or from parts thereof. The sinter blanks in the prior art can be made both of ceramic and also of metallic materials. The sintering process itself practically always involves a shrinking process. Moreover, the as yet unsintered material, or the sinter blank, is a not very stable material. The final material strength is achieved only through at least one sintering process. The sintering temperatures are relatively close to the melting point of the material, such that the shaped body to be sintered, or sinter blank, is very sensitive until the conclusion of the sintering process.

Especially in the case of quite large sinter blanks, or of dental prostheses to be produced from these, it has in practice been found difficult to ensure a sintering process that is free of distortion. Undesirable deformations often occur through warping. It has therefore already been attempted in practice to integrate struts into the sinter blanks in order to support the product area, i.e. the part of the sinter blank from which the subsequent dental prosthesis is obtained.

SUMMARY

The object of the invention is to further improve sinter blanks of the abovementioned type such that the sinter blank is able to be sintered in a way that is as free as possible from distortion.

This is achieved by a sinter blank having one or more features of the invention.

Provision is thus made that the strut has at least one sliding knob for supporting the strut on a base surface during the sintering process.

The at least one sliding knob according to the invention on the strut has the effect, on the one hand, that the strut itself is supported on the base surface during the sintering process. In this way, the inherent weight of the strut does not load the product area of the sinter blank. In addition, during the sintering-induced shrinkage of the sinter blank, the sliding knob is able to slide across the base surface in order to permit shrinkage of the sinter blank in a manner as free as possible from distortion. Compared to the case where the full area of the strut lies on the base surface, the sliding knob greatly reduces the kinetic and static friction resistance of the strut.

The sinter blank is also often designated as a green body. It is in most cases comprised of compacted starting material or powder. Sinter blanks according to the invention can be comprised of or produced from both ceramic and metallic materials. In the sinter blank, the product area and the strut and, if appropriate, any other component parts are generally connected integrally to one another. Generally, all parts of the sinter blank are formed of the same starting material or the same composition of the starting material. The sinter blank can be a blank that is still completely unsintered. However, it can also be that the sinter blank is already partially sintered or pre-sintered and has to be completely sintered in the sintering process or in further sintering processes. The product area of the sinter blank is the part of the sinter blank from which the dental prosthesis is later obtained. Generally, the product area already has a similar shape to the dental prosthesis. However, since shrinkage of the material has to be taken into consideration in sintering, the product area generally has correspondingly greater dimensions than the finally sintered dental prosthesis. Moreover, after the sintering, the dental prosthesis may in particular undergo secondary processing, e.g. in order to remove the strut and/or the support feet mentioned below, as a result of which differences in shape can in turn arise between product area and dental prosthesis. The strut serves exclusively to support or stiffen or brace the product area during the sintering process. The strut itself is no longer to be seen on the final product, i.e. on the finished dental prosthesis, since it is separated from the product area, ground off or otherwise removed after the sintering process. In any case, the product area and the strut with the at least one sliding knob are already formed in the sinter blank and are thus visually discernible as such. The expression dental prostheses basically includes all artificial parts that replace the corresponding natural parts of the dentition in the mouth of the patient. They can therefore be artificial teeth, parts of artificial teeth, but especially also dental arches, bridges and the like. In this context, in particularly preferred embodiments of the invention, provision is made that the product area is a dental arch with a plurality of teeth interconnected preferably in pairs, and the strut connects at least two teeth of this dental arch to each other. Particularly preferably, provision is made that the dental arch partially encloses an interior, and the strut is arranged at least partially in the interior. However, dental prostheses can also be auxiliary devices that serve in the production or securing of artificial teeth, bridges, dental arches or the like in the mouth of the patient. In this context it will be noted that, when teeth and dental arches are mentioned here, these signify artificial teeth and dental arches, unless otherwise evident from the context.

The expression sliding knob designates an elevation on a corresponding surface of the strut, with which the strut can better slide on a base surface during the sintering process, such that shrinkage occurring in the product area and in the strut does not lead to distortion. The sliding knob, and also its bearing surface mentioned below, can have very different shapes and sizes, e.g. rod-shaped or cone-shaped or hemispherical. The base surface is the surface on which the sinter blank is supported during the sintering process.

In preferred embodiments of the invention, especially in the case of quite large struts, provision is made that the strut has a plurality of sliding knobs arranged at a distance from one another for supporting the strut on the base surface during the sintering process. Here, and as it is also used further below, the expression "a plurality of" in principle includes a number of two and more.

To keep the friction against the base surface to a minimum, provision is preferably made that the or each individual sliding knob for supporting the strut on the base surface during the sintering process has a reduced bearing surface in relation to the strut. Reduced bearing surface in relation to the strut signifies that the bearing surface of the sliding knob, i.e. the surface with which the sliding knob lies on the base surface in the operational position, i.e. during sintering, is smaller than the surface with which the strut would lie on the base surface in the operational position if no sliding knob were present. In preferred embodiments, the bearing surface of the sliding knob(s) is as small as possible. The bearing surface of the sliding knob(s) is thus preferably reduced, preferably in each case, to a bearing point. The expression bearing point is used when the bearing surface is so small that it appears as a point to the human eye. In the case where a plurality of sliding knobs are present on the strut, it is preferable that the sliding knobs, or preferably each of the sliding knobs, for supporting the strut on the base surface during the sintering process have/has a reduced bearing surface in relation to the strut, preferably a bearing point. This expediently also applies to the sum of all the bearing surfaces of all the sliding knobs on a strut. Moreover, the sum of these bearing surfaces is preferably smaller than the surface with which the strut would lie on the base surface in the operational position if no sliding knobs were present.

During the sintering, the shrinkage process occurring on the sinter blank has the effect that different parts and areas of the sinter blank are moved in mutually different directions. To ensure a sliding movement of the sliding knob in all directions equally well and thus to be able to compensate for shrinkage processes in all directions equally well, preferred embodiments of the invention provide that the bearing surface of the sliding knob is a bearing point. If this is not the case, it is expedient if the bearing surface of the sliding knob has a maximum width and a maximum length which are as far as possible the same. The maximum width of the bearing surface differs expediently by at most 50% from the maximum length of the bearing surface. In this context, a circular or annular bearing surface is particularly expedient. However, the bearing surface can also have other shapes, e.g. a square or triangular shape or the like. The bearing point or the bearing surface of the sliding knob is in any case the area of the sliding knob with which the sliding knob lies on the base surface in the operational position.

To be able also to support the product area as well as possible on the base surface, in preferred embodiments of the invention provision is made that, on the product area, the sinter blank has a support foot, or a plurality of support feet arranged at a distance from one another, for supporting the product area on the base surface during the sintering process. Since the support feet generally have to be removed from the product area by grinding after the sintering process, they expediently have a pin-shaped configuration. However, they can equally be configured like the sliding knobs, e.g. also hemispherical or conical. To ensure that the support foot or support feet are also able to slide across the base surface with the least possible resistance during the sintering process, preferred embodiments of the invention are ones in which the support foot or the support feet for supporting the product area on the base surface during the sintering process preferably has, or preferably in each case have, a reduced bearing surface in relation to the product area, preferably a bearing point. The punctiform or circular bearing surfaces of the support feet here serve the same purpose as in the sliding knobs. Therefore, in terms of their shape and size, the observations made above with respect to the bearing surfaces of the sliding knobs also apply.

In preferred embodiments, provision is made that the base surface is a plane. Particularly preferably, provision is made that all the bearing points and/or bearing surfaces of all the sliding knobs and also of all the support feet, if the latter are present, are arranged in a common plane.

To ensure that the sliding knobs and if appropriate also the support feet slide along with the least possible friction during the sintering-induced shrinkage of the sinter blank, the invention also makes available a sintering chamber for sintering at least one sinter blank according to the invention, wherein the sintering chamber has a plane sliding surface as base surface on which to place the sinter blank during the sintering process. In particularly preferred embodiments, a sintering chamber with at least one sinter blank according to the invention is provided. These embodiments are as it were an arrangement with a sintering chamber and with at least one sinter blank according to the invention, wherein the sintering chamber likewise has a plane sliding surface as base surface for placing the sinter blank on this base surface during the sintering process. During the sintering process, the sinter blank is expediently placed on this base surface. The base surface can be a separate component, e.g. a separate disk, which is inserted into the sintering chamber. However, it is also conceivable to design the bottom of the sintering chamber directly as this base surface. The base surface, for forming a plane sliding surface, can be made of a high-temperature-resistant ceramic material, e.g. zirconium dioxide, aluminum oxide or silicon carbide. However, the base surface can also be made from suitable metals or metal alloys. For the purpose of good sliding properties, the surface can be, for example, a finely ground, ultra-finely ground or also polished surface. The base surface can itself be obtained by a sintering process, if appropriate with subsequent fine grinding, ultra-fine grinding or polishing. The plane sliding surface expediently has a mean roughness Ra of finer than 3 µm (micrometers), preferably finer than 0.2 µm, particularly preferably finer than 0.1 µm, according to DIN EN ISO 4287.

With respect to the sintering chamber, it will also be noted that this expression is to be interpreted in its broadest sense. It is any chamber in which sintering can take place. For example, it can be the sintering furnace itself. However, it can also be a separate chamber, for example, which is introduced into a sintering furnace for sintering purposes. The use of a separate chamber can be exploited, for example, to ensure that the sinter blank is sintered in a protective gas atmosphere generated in the sintering chamber.

In a method for sintering a sinter blank according to the invention, provision can be made that the sinter blank, during the sintering in a sintering chamber, slides with its sliding knob or its sliding knobs and with, if present, its support foot or support feet on a base surface which is formed as a plane sliding surface in the sintering chamber in order to permit shrinkage of the sinter blank in a manner that is as free as possible from distortion.

In a method for constructing and/or producing a sinter blank according to the invention, provision is made that at least one sliding knob is integrally formed on the strut, with which the strut can be supported or is supported on the base surface during the sintering process.

In preferred embodiments of the invention, this construction and/or production method is carried out using at least one corresponding computer program. To this extent, the invention also relates to a computer program for constructing at least one sinter blank according to the invention on a digital data processor. Such a computer program is preferably a development of CAD programs known per se, wherein it is likewise preferable that at least one sliding knob is integrally formed on the strut during the construction of the sinter blank, with which sliding knob the strut can be supported on the base surface during the sintering process. The choice of the number, shape, size and/or position of the sliding knobs on the strut can be made in an automated manner by this computer program. It is equally possible that the user of the computer program inputs these parameters individually. It is also possible that the computer program offers a proposal concerning these parameters, i.e. the number, shape, size and/or position of the sliding knobs on the strut, and the user of the computer program can then review this proposal. The computer program can preferably also construct all the above-mentioned preferred features of the sinter blank. The sinter blank constructed by the computer program then expediently is present in digital form. It is preferably used to drive a device known per se for removing material from a block of starting material, such that the device for removing material is then able, on the basis of the result of the computer program, to work the sinter blank from the block of starting material. To this extent, the invention can also relate to a device for removing material from a block of starting material, wherein provision is made that the device works the sinter blank according to the invention, constructed by the computer program, from the block of starting material. Machining by removal of material is understood in particular as milling and/or grinding.

BRIEF DESCRIPTION OF THE DRAWINGS

Further features and details of preferred embodiments of the invention are explained by way of example on the basis of the schematic illustrations in which.

DETAILED DESCRIPTION OF THE PREFERRED EMBODIMENTS

Figure 1:
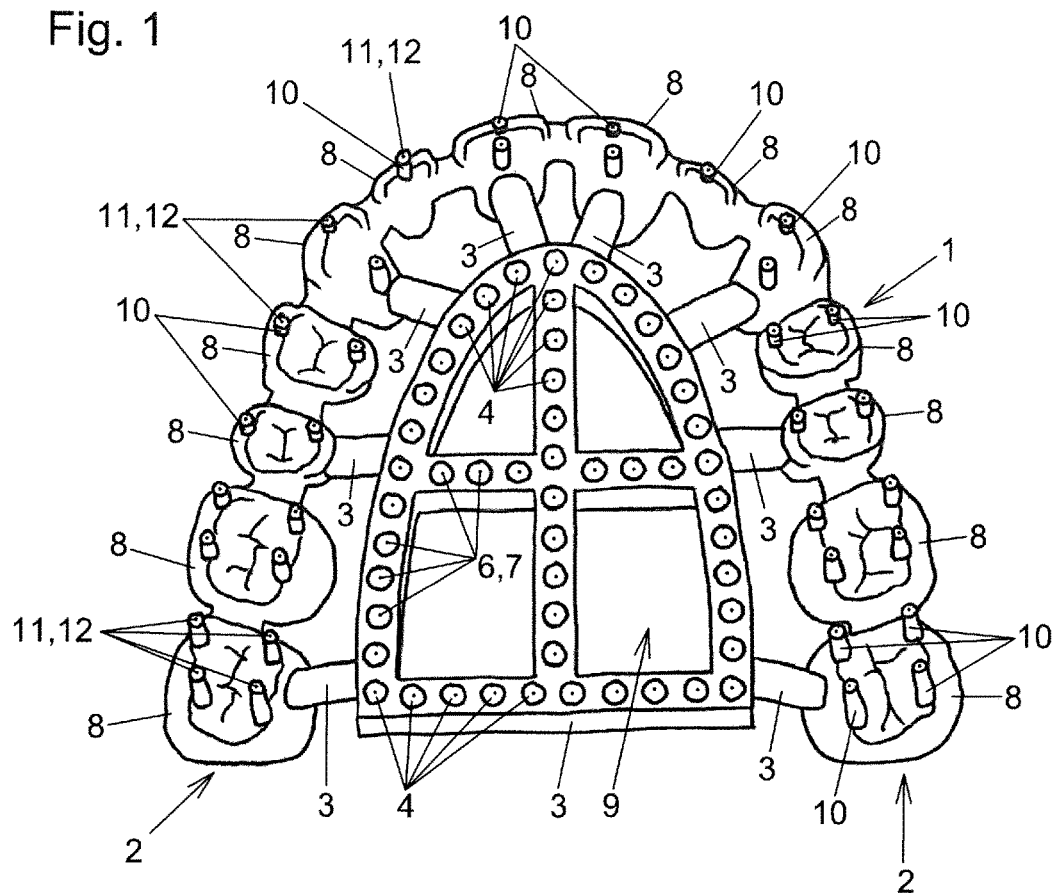
FIG. 1 shows a bottom view of a first sinter blank according to the invention.
Figure 2:
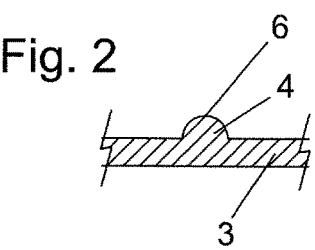
FIGS. 2 and 3 show cross-sectional views through a strut in the area of sliding knobs of different shapes.
Figure 3:
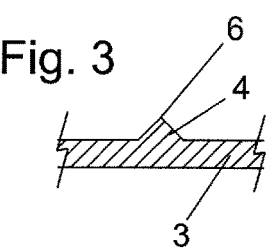

FIG. 1 shows a bottom view of a sinter blank 1, i.e. a view of the underside via which the sinter blank 1 stands on the base surface 5 during sintering. In this illustrative embodiment according to FIG. 1, the product area 2, i.e. the area of the sinter blank 1 from which the dental prosthesis is obtained, is designed as a complete dental arch with a corresponding number of teeth 8. The strut 3 of the sinter blank 1 connects a plurality of teeth 8 of this dental arch to one another, in order to make the sinter blank 1 as a whole more stable and to avoid distortion in the sintering process as far as possible. According to the invention, the strut 3 has sliding knobs 4 for supporting the strut 3 on the base surface 5 during the sintering process. Each of the sliding knobs 4 has a bearing point 6, or as small of a bearing surface 7 as possible, with which to be placed on the base surface 5 during the sintering process. Examples of possible embodiments of the sliding knobs are shown in FIGS. 2 and 3, each in a cross-sectional view through the strut 3. In FIG. 2, the sliding knob 4 has a hemispherical shape with a punctiform bearing point 6. In FIG. 3, a cone-shaped sliding knob 4 is shown as an example. This too has a punctiform bearing point 6. A circular or annular bearing surface 7 can of course also be obtained by suitable flattening of the sliding knobs 4.

It can be seen clearly from FIG. 1 that the dental arch comprised of the teeth 8, and here forming the product area 2, encloses an interior 9 in which the strut 3 is arranged.

To be able also to support the product area 2 directly on the base surface 5, the sinter blank 1 in the illustrative embodiment shown in FIG. 1 has, on the product area, a plurality of support feet 10 which are arranged at a distance from one another and with which the product area 2 can be supported on the base surface 5 during the sintering process. The support feet 10, designed here with a pin shape for example, also have the smallest possible bearing surface, i.e. bearing points 11 or the smallest possible bearing surfaces 12, with which they are then supported on the base surface 5 in the operational position during the sintering process. After the sintering process, both the strut 3 and the support feet 10 are removed from the product area 2 by suitable measures known per se in the prior art, such that the desired dental prosthesis is then made ready, if appropriate after further secondary processing steps.

Figure 4:
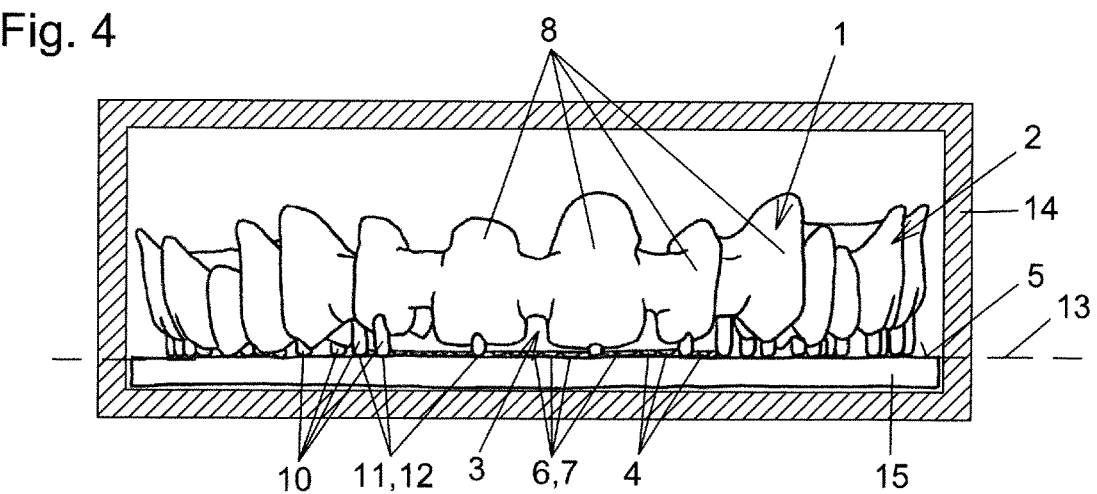
FIG. 4 shows a schematic illustration of a sintering chamber with a base surface arranged therein and with a sinter blank as per FIG. 1 placed on the base surface.

FIG. 4 is a highly schematic illustration of a sintering chamber 14 in which the sinter blank 1 from FIG. 1 is supported on the base surface 5 in the operational position during the sintering process. The base surface 5 is in this case expediently a plane sliding surface, as has been explained in more detail above. In this preferred illustrative embodiment, the sliding knobs 4 and the support feet 10 all rest with their bearing points 6 and 11, respectively, or their bearing surfaces 7 and 12, respectively, on a common plane 13 of the base surface 5 formed by the corresponding plane sliding surface. In the illustrative embodiment shown, the base surface 5 is a surface of a for example ceramic, polished disk 15, which is inserted into the sintering chamber 14. However, it can equally be configured such that the base surface 5 is formed directly by a corresponding bottom surface of the sintering chamber 14. As regards the basic structure of a sintering chamber 14, reference may be made to the prior art, and it will therefore not be discussed in any more detail here. This also applies in particular to the various possibilities of feeding and discharging protective gas into the sintering chamber 14 in order, during the sintering process, to create within the sintering chamber 14 an atmosphere that is as free as possible from oxides, if this is necessary.

Figure 5:
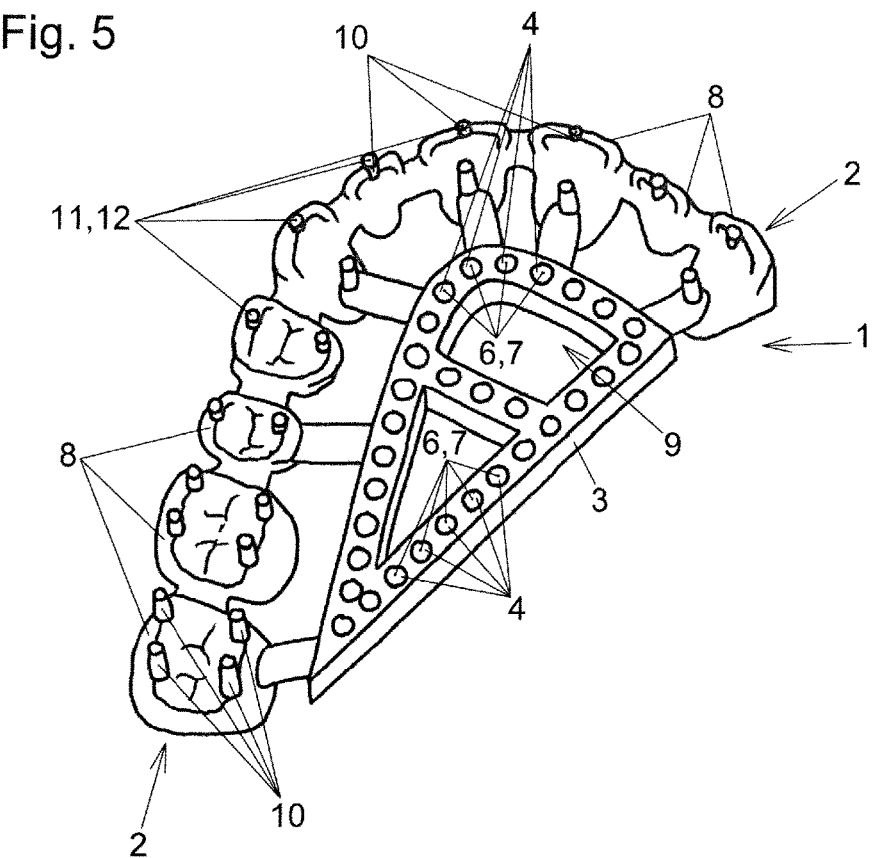
FIGS. 5 and 6 show further examples of sinter blanks configured according to the invention.
Figure 6:
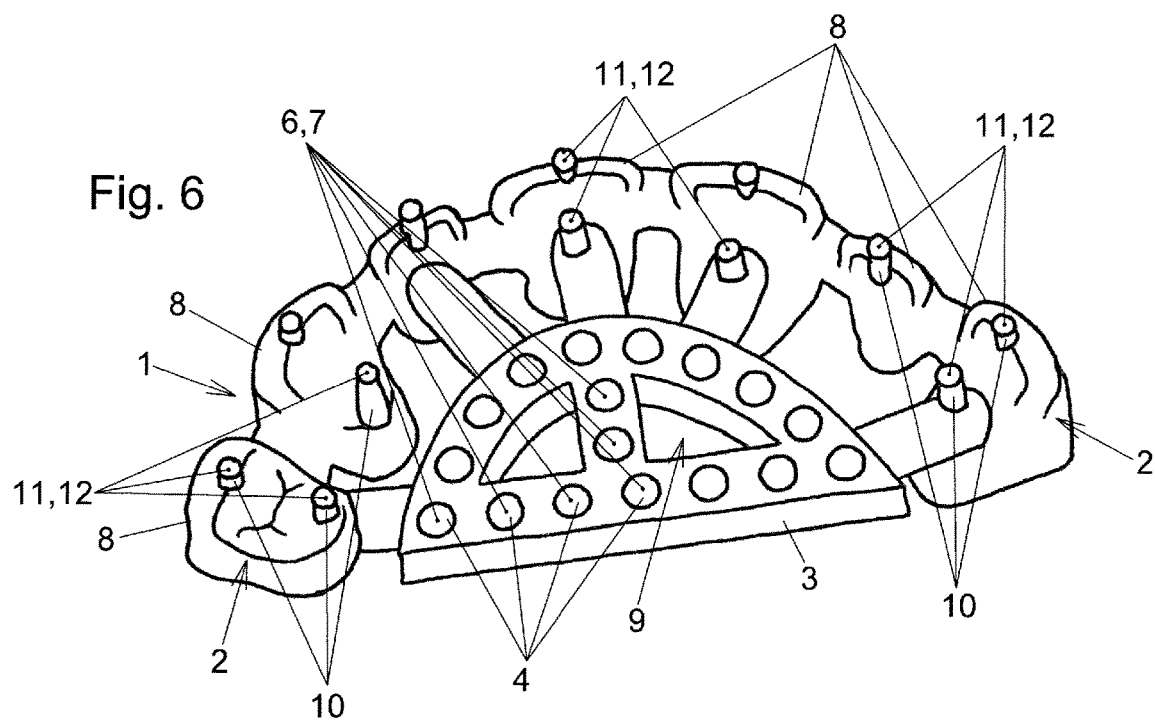

FIGS. 5 and 6 show examples of further sinter blanks in which the product area 2 is also comprised of a sequence of teeth 8, but not those of a complete dental arch, instead only of a dental arch that replaces only some of the natural teeth of the natural dental arch. In these sinter blanks 1 as well, provision is made according to the invention that the strut 3 has corresponding sliding knobs 4. Corresponding support feet 10 are also arranged on the product area 2. Otherwise, the observations concerning the first variant according to FIG. 1 also apply to these illustrative embodiments.

KEY TO THE REFERENCE NUMBERS 1 sinter blank
2 product area
3 strut
4 sliding knob
5 base surface
6 bearing point
7 bearing surface
8 tooth
9 interior
10 support foot
11 bearing point 12 bearing surface
13 common plane
14 sintering chamber
15 disk

The invention claimed is:

1. A sinter blank for producing a dental prosthesis in at least one sintering process, the sinter blank comprising at least one product area, from which the dental prosthesis is obtained, and at least one strut, which is adapted to be removed after the sintering process, the strut has at least one sliding knob that is part of the strut and that is adapted to support the strut on a base surface during the sintering process.

2. The sinter blank as claimed in claim 1, wherein the strut has a plurality of sliding knobs arranged at a distance from one another that are adapted to support the strut on the base surface during the sintering process.

3. The sinter blank as claimed in claim 1, wherein the sliding knob for supporting the strut on the base surface during the sintering process has a reduced bearing surface in relation to the strut.

4. The sinter blank as claimed in claim 1, wherein the product area is a dental arch with a plurality of teeth interconnected to one another, and the strut connects at least two teeth of said dental arch to each other.

5. The sinter blank as claimed in claim 4, wherein the dental arch partially encloses an interior area, and the strut is arranged at least partially in the interior area.

6. The sinter blank as claimed in claim 1, wherein, on the product area, the sinter blank has a support foot that is adapted to support the product area on the base surface during the sintering process.

7. The sinter blank as claimed in claim 6, wherein the support foot that is adapted to support the product area on the base surface during the sintering process has a reduced bearing surface in relation to the product area.

8. The sinter blank as claimed in claim 2, wherein the sliding knobs for supporting the strut on the base surface during the sintering process each have a reduced bearing surface in relation to the strut.

9. A sintering chamber for sintering at least one sinter blank according to claim 1, the sintering chamber comprising a plane sliding surface as base surface that the at least one sinter blank is placed on during the sintering process.

10. A computer program for constructing at least one sinter blank as claimed in claim 1, comprising computing steps recorded on a fixed computer readable medium that run on a digital data processor.

11. The sinter blank as claimed in claim 8, wherein all the bearing surfaces of all the sliding knobs are arranged in a common plane.

12. The sinter blank as claimed in claim 8, wherein the reduced bearing surface is a bearing point.

13. The sinter blank as claimed in claim 6, wherein a plurality of the support feet (10) arranged at a distance from one another are provided.

14. The sinter blank as claimed in claim 7, wherein the reduced bearing surface is a bearing point.

15. The sinter blank as claimed in claim 11, wherein on the product area, the sinter blank has a support foot that is adapted to support the product area on the base surface during the sintering process, and the support foot is arranged in the common plane.

* * * * *